(12) United States Patent
Senosiain Peláez et al.

(10) Patent No.: US 8,846,708 B2
(45) Date of Patent: Sep. 30, 2014

(54) SALT OF A PYRIMIDIN DERIVATIVE

(75) Inventors: Juan Pablo Senosiain Peláez, Distrito Federal (MX); Héctor Senosiain Arroyo, Distrito Federal (MX); Manuel Francisco Lara Ochoa, Distrito Federal (MX)

(73) Assignee: Laboratorios Senosiain S.A. de C.V., Distrito Federal (MX)

( * ) Notice: Subject to any disclaimer, the term of this patent is extended or adjusted under 35 U.S.C. 154(b) by 0 days.

(21) Appl. No.: 13/877,887

(22) PCT Filed: Oct. 4, 2011

(86) PCT No.: PCT/IB2011/054369
§ 371 (c)(1),
(2), (4) Date: Apr. 30, 2013

(87) PCT Pub. No.: WO2012/046193
PCT Pub. Date: Apr. 12, 2012

(65) Prior Publication Data
US 2013/0210848 A1  Aug. 15, 2013

(30) Foreign Application Priority Data
Oct. 6, 2010 (MX) .................... MX/a/2010/011006

(51) Int. Cl.
*A01N 43/42* (2006.01)
*A61K 31/44* (2006.01)
*C07D 239/42* (2006.01)
*C07D 233/64* (2006.01)
*C07D 239/69* (2006.01)
*C07C 229/26* (2006.01)

(52) U.S. Cl.
CPC ............ *C07D 239/69* (2013.01); *C07D 239/42* (2013.01); *C07D 233/64* (2013.01); *C07C 229/26* (2013.01)
USPC ......................................... 514/275; 544/297

(58) Field of Classification Search
USPC .......................................... 544/297; 514/275
See application file for complete search history.

(56) References Cited

U.S. PATENT DOCUMENTS 5,260,440 A * 11/1993 Hirai et al. .................... 544/332
2005/0131066 A1* 6/2005 Niddam-Hildesheim et al. ............................. 514/548

FOREIGN PATENT DOCUMENTS

| WO | WO 03/082816 A1 | 10/2003 |
| WO | WO 2005/046575 A2 | 5/2005 |
| WO | WO 2006/126035 A2 | 11/2006 |
| WO | WO 2007/089745 A2 | 8/2007 |

OTHER PUBLICATIONS

L.D. Bighley et al., Salt Forms and Absorption, in 13 Encyclopedia of Pharmaceutical Technology 453 (M Swarbrick and J. Boylan eds., 1996).*
R. J. Bastin et al., 4 Organic Process Research & Development, 427-436 (2000).*
S. H. Neau, Pharmaceutical Salts, in Water-Insoluble Drug Formulation 417, 429 (R. Liu ed., CRC Press, 2008).*
P.L. Gould, Salt Selection for Basic Drugs, 33 Int. J. Therapeutics 201, 217 (1986).*
K. R. R Morris et al., An Integrated Approach to the Selection of Optimal Salt Form for a New Drug Candidate, 105 Int'l. J. Pharm. 209 (1994).*
K. Chow et al., Engineering of Pharmaceutical Materials: an Industrial Perspective, 97 J. Pharmaceutical Sciences, 2855 (2008).*
S.L. Morissette et al., Advanced Drug Delivery Reviews, 56, 275-300 (2004).*
S.R. Vippagunta et al., Advanced Drug Delivery Reviews, 48, 3-26 (2001).*
J.K. Guillory, Generation of Polymorphs, Hydrates, Solvates, and Amorphous Solids, in Polymorphism in Pharmaceutical Solids 183-220 (H.G. Brittain ed., 1999).*

* cited by examiner

*Primary Examiner* — James O Wilson
*Assistant Examiner* — Alexander R Pagano
(74) *Attorney, Agent, or Firm* — Birch, Stewart, Kolasch & Birch, LLP

(57) ABSTRACT

The present invention relates to a salt of a pyrimidin derivative of the acid (3R,5S,6E)-7-[4-(4-fluorophenyl)-2-(N-methylmethanesulfonamide)-6-(propan-2-yl)pyrimidin-5-yl]-3,5-dihydroxyhept-6-enoic, to a method for preparing same and to the use thereof in formulating pharmaceutical formulations.

6 Claims, 6 Drawing Sheets

SALT OF A PYRIMIDIN DERIVATIVE

FIELD OF THE INVENTION

The present invention comprises a salt of a pyrimidic derivative, more particularly a salt of (3R,5S,6E)-7-[4-(4-fluorophenyl)-2-(N-methylmethanesulfonamide)-6-(propan-2-yl)pyrimidin-5-yl]-3,5-dihydroxihept-6-enoic acid, as well as a procedure for its preparation and the use of said salt for the manufacture of pharmaceutical formulations.

BACKGROUND OF THE INVENTION

Cardiovascular diseases and dyslipidemia disorders are currently recurring conditions for which there are different drugs such as statins, fibrates and combinations thereof.

Rosuvastatin, a pyrimidin derivative, is an inhibitor of 3-hydroxy-3-methylglutaryl coenzime A (HMG-CoA) reductase, which catalizes the conversion of HMG-CoA to mevalonate, limiting initial step of cholesterol biosynthesis. It has a relative hydrophilic capacity. Its metabolism is independent of Cytochrome P450 (CYP), presenting less pharmaceutical interactions than atorvastatin and simvastatin.

Rosuvastatin is mainly used as calcium salt (formula I). This salt has an absolute bioavailability of approximately 20%, it binds to proteins in an 88%, reaching a maximum peak between 3 and 5 hours. It is mainly excreted in feces (90%) and urine (10%), with a half-life of 19 hours.

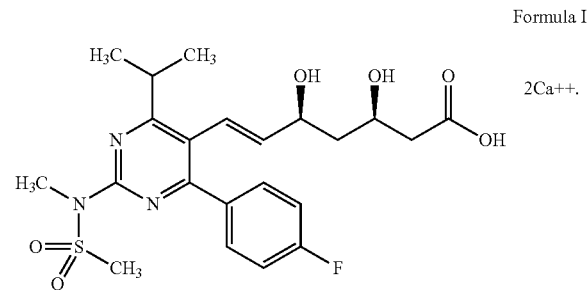 [SMILES: CC(C)c1nc(N(C)S(C)(=O)=O)nc(-c2ccc(F)cc2)c1/C=C/[C@@H](O)C[C@@H](O)CC(=O)O]

Formula I

Rosuvastatin is slightly soluble in water, not very stable in extreme environmental conditions, is a compound with acidic characteristics, therefore it is mainly associated to compounds with alkaline characteristics such as metallic salts of calcium, zinc, strontium, sodium, magnesium, lithium, among others. It can be seen from different publications on rosuvastatin that problems arise during the synthesis process to obtain rosuvastatin salts and during purification and crystallization processes. From the above it is displayed that the problem of obtaining stable salts, that may be used for producing physicochemically stable compositions, has not been solved.

U.S. Pat. No. 5,260,440, (USRE37314-Shionogi) describes the synthesis of (3R,5S,6E)-7-[4-(4-fluorophenyl)-2-(N-methyl methanesulfonamide)-6-(propan-2-yl)pyrimidin-5-yl]-3,5-dihydroxihept-6-enoic acid, commonly known as rosuvastatin. This patent describes a complex process for obtaining rosuvastatin with diastereoisomeric impurities. In contrast, in this invention a new salt of rosuvastatin with improved stability and solubility properties without diastereoisomeric impurities is obtained.

International application WO2000/042024 describes processes for obtaining amorphous rosuvastatin, where rosuvastatin impurities are obtained in lower amount, in comparison to the process disclosed in U.S. patent '440. Unlike in this invention, the process of application WO2000/042024 is characterized by a purification method for rosuvastatin to obtain calcium rosuvastatin, and rosuvastatin is not in the form of an amino acid salt, as is the objective of the present invention.

WO2001/060804-ASTRAZENECA (Mexican Application PA/a/2002/000781, U.S. Pat. No. 6,841,554) describes the preparation of crystalline salts of rosuvastatin in order to solve technical problems of the process disclosed in U.S. Pat. No. 5,260,440. These crystalline salts are more easily purified in comparison to an amorphous form, they are more physicochemically stable and more resistant to oxidative degradation. This document mentions the development of rosuvastatin salts of ammonium, methylammonium, ethylammonium, diethylammonium, tris(hydroxymethyl)methylammonium, benzylammonium, 4-metoxibenzylammonium, lithium or magnesium salt. This document refers to stable salts where the anion is a metal or an ammonium compound, unlike the present invention which refers to stable salts with amino acid.

ASTRA's WO2004/014872 (Mexican Appl. PA/a/2005/001582, U.S. Pat. No. 7,511,140) describes the preparation of a rosuvastatin calcium salt that demonstrates effectiveness in its synthesis process, particularly in the filtration step, characterized in that a calcium chloride salt is mixed with a solution of rosuvastatin sodium salt soluble in water. This is an improvement in the process of obtaining the rosuvastatin calcium salt, however the described salt do not correspond to the salts of the present invention.

TEVA's U.S. Pat. No. 7,582,759 (Mexican Application MX/a/2007/037979, WO2006091770, EP1737829), describes the preparation of rosuvastatin intermediaries and salts thereof, it comprises the use of an alcohol of the methanol kind, with an organic solvent and an hydride ion source. A pure enantiomeric salt of rosuvastatin is obtained, excluding salts formed with amino acids.

MX/a/2007/009281—Lifecycle Pharma A/S (WO06084474, US2008131503), presents an oral composition comprising a mixture combining fenofibrate and a HMG-CoA reductase compound, in separate entities in a single dosage form. HMG-CoA reductase is a statin selected from the group of atorvastatin, lovastatin, pravastatin, simvastatin, rosuvastatin, fluvastatin and pitavastatin, being atorvastatin the preferred one. Unlike this formulation, the present invention provides a rosuvastatin stable salt with improved solubility, as well as its method of synthesis and obtention thereof.

WO06126035-Richter Gedeon Vegyészeti Gyár Rt. HU (EP1902036B) refers to a rosuvastatin calcium preparation process starting from (6-{(E)-2[4-(4-fluorophenyl)-6-isopropyl-2-(methanesulfonyl-methyl-amino)pyrimidin-5-yl]-vinyl}-(4R,6S)-2,2-dimethyl-[1,3]dioxan-4-yl) acetic acid, which may preferably presented as salt formed with diethanolamine, L-lysine or magnesium. These salts are reacted with calcium chloride in the presence of an alkali to remove the acetonide group and to obtain calcium rosuvastatin as final product. Unlike this formulation, the present invention provides a process for obtaining a rosuvastatin lysine salt instead of the rosuvastatin calcium salt without starting from an intermediary and in a shorter time than the synthesis process described in the patent WO06126035.

WO07089745—Signature R & D Holdings Llc (U.S. Pat. No. 7,589,233), refers to a method for improving at least one therapeutic property of an active ingredient by combining an amino acid and an active ingredient. Compositions preferably may be the combination of a L-threonine derivative and an active ingredient selected from different therapeutic groups, one of which groups can be rosuvastatin, resulting in the physical combination of threonine and rosuvastatin. The present invention relates to the synthesis of a rosuvastatin lysine salt, where the salt thereby obtained has better solubility and physicochemical stability properties, and is useful for preparing a medicament.

WO2006/136407 Lek Pharm. (US2009111839, EP1912952A) describes a process for preparing a pure form of amorphous rosuvastatin with a purity ranging from 99.5% to 99.9%, wherein the process is carried out through hydrolysis of C1-C5 of the rosuvastatin alkyl ester, preferably rosuvastatin tert-butyl ester with a nitrogenous base such as guanidine, amidine, amines and quaternary ammonium hydroxides in the presence of water or an aprotic solvent.

Rosuvastatin in its basic form and amorphous rosuvastatin salts are very unstable and slightly soluble in aqueous solutions, therefore it is an objective of this invention to present a rosuvastatin salt with improved solubility and stability properties. There are different rosuvastatin salts as well as new purification processes of these salts. The existing salts of rosuvastatin are basic salts and mineral salts such as magnesium, lithium, aluminum, zinc, strontium, among others, and can be amorphous or non-amorphous salts. Their manufacture methods occur through complex processes with organic solvents, filtration, drying, re-crystallization processes and others that increase operating time as well as their manufacture cost.

The present invention provides a new rosuvastatin salt which is more stable and more soluble than the available rosuvastatin salts, for the elaboration of pharmaceutical compositions.

Justification of the Invention

For the production of rosuvastatin salts with magnesium, lithium, aluminum, zinc, strontium and calcium there are different processes that, to date, still have the problem of rendering diastereoisomeric impurities, besides they present solubility problems during the elaboration of pharmaceutical forms. Therefore, there is a need of a process for obtaining a rosuvastatin salt with less by-products, wherein the salt is stable for preparing a pharmaceutical composition which is physicochemically stable and useful for treating cardiovascular diseases.

The present invention provides a rosuvastatin amino acid salt with improved aqueous solubility and more physicochemical stability, which provides more absolute bioavailability and improved pharmacokinetics when preparing a pharmaceutical composition.

However, it is not possible to obtain this salt by simple association of rosuvastatin with any amino acid, since particular conditions must be created during the production process, such as selecting appropriate raw materials, atmosphere, temperature, moisture, pH; an example of this situation, contrary to what might be expected, is that it is not possible to produce the salt with arginine.

The present invention comprises a rosuvastatin salt with an amino acid that can be lysine or histidine, in a non limiting way.

The rosuvastatin salt of this invention can be obtained with good yield and good purity, so that it is specially suitable for the manufacture of pharmaceutical formulations.

The rosuvastatin lysine salt of this invention offers better flowability compared to the calcium salt. This property provides better conditions for preparing a pharmaceutical composition.

In the solubility assay, the rosuvastatin-lysine salt of the present invention exhibits a greater and better aqueous solubility, being of 218 mg/mL versus 5.3 mg/mL of rosuvastatin calcium, which represents an increased solubility by just over 40%. This property allows it to be more bioavailable within the organism when being presented in pharmaceutical compositions.

BRIEF DESCRIPTION OF DRAWINGS

The figures illustrate the characterization result of the rosuvastatin-lysine salt.

DETAILED DESCRIPTION OF THE INVENTION

The present invention consists of a process for obtaining a stable rosuvastatin salt, of high purity, with improved solubility that allows for the manufacture of a pharmaceutical composition with stability in the process and during shelf-life, which allows it to preserve its therapeutic properties as long as possible. Coupled with this, the solubility enhancement in aqueous media facilitates the bioavailability within the organism once presented in a pharmaceutical form.

Synthesis Method for the New Rosuvastatin Salt

A scheme for the synthesis of the rosuvastatin-amino acid salt of the present invention is illustrated below. As an example, the scheme presents the way of obtaining the rosuvastatin lysine salt of Formula II.

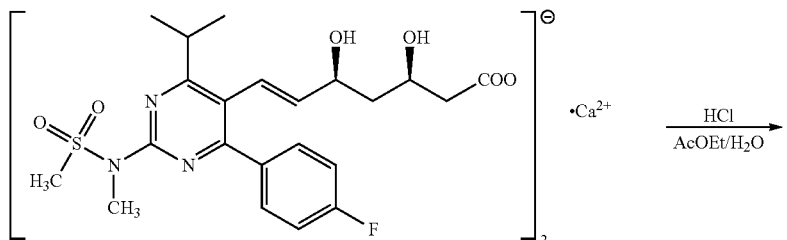

Formula I

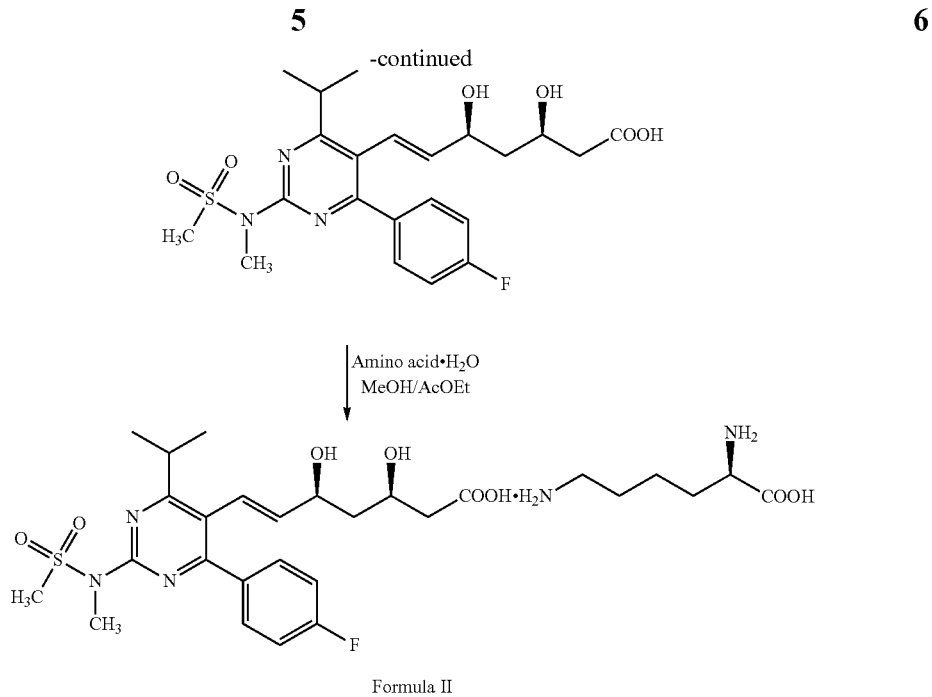

Formula II

Diagram of the Synthesis Process of the Rosuvastatin Amino Acid Salt

In this invention for obtaining a rosuvastatin amino acid salt the starting substance is rosuvastatin calcium salt (Formula I), this salt is subjected to a dissociation process in the presence of an ethyl acetate/water solution and hydrochloric acid.

The resulting acid rosuvastatin is mixed with an aqueous solution containing the selected amino acid for producing the new salt, in the presence of a methanol/ethyl acetate solution.

To stabilize the combination, the reaction medium is kept under constant stirring.

Finally a rosuvatatin amino acid salt is obtained through a non covalent bond, this new salt is stable and presents an improved aqueous solubility compared to the rosuvastatin calcium salt.

The lysine rosuvastatin salt (Fórmula II) obtained by the process of the present invention was subjected to identification and stability assays which demonstrate that the salt is useful for preparing a pharmaceutical composition.

Identity Analysis

Figure 1:
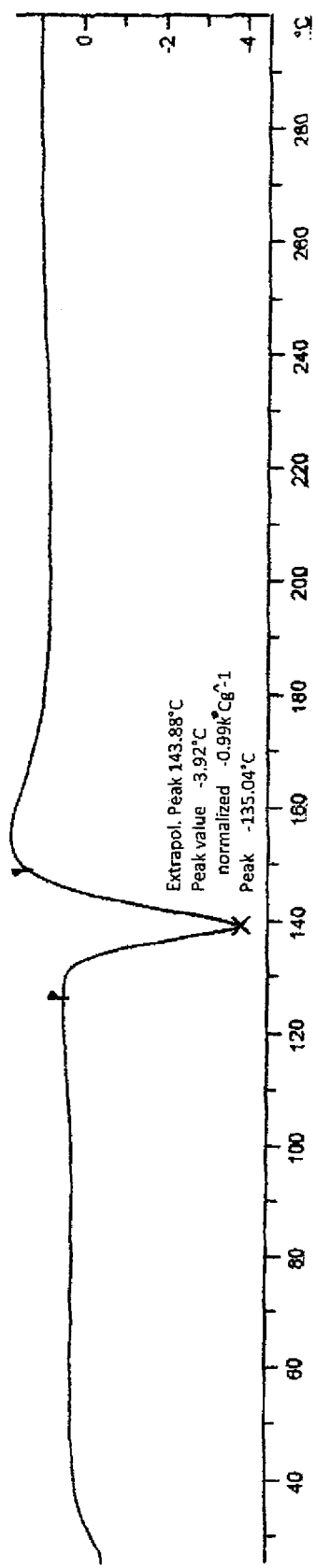
FIG. 1. Differential thermal spectrum (DSC)
Figure 2:
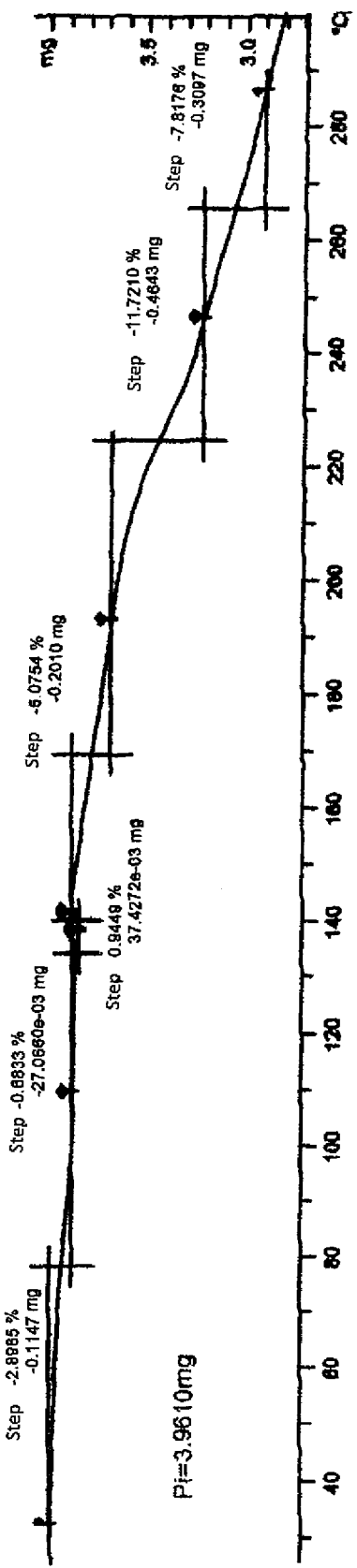
FIG. 2. Thermogravimetric analysis spectrum (TGA).

Differential Thermal Analysis DSC and Gravimetric Thermal Analysis TGA-DTG (FIGS. 1 and 2). These analysis determined the weight loss of the analyzed sample. The result shows a weight loss of 2.9% which starts at 30° C. and ends at 115° C. This corresponds to the loss of a mole of water, in addition another weight loss begins at 190° C. and ends at 290° C., which corresponds to the lysine decomposition.

Figure 3A:
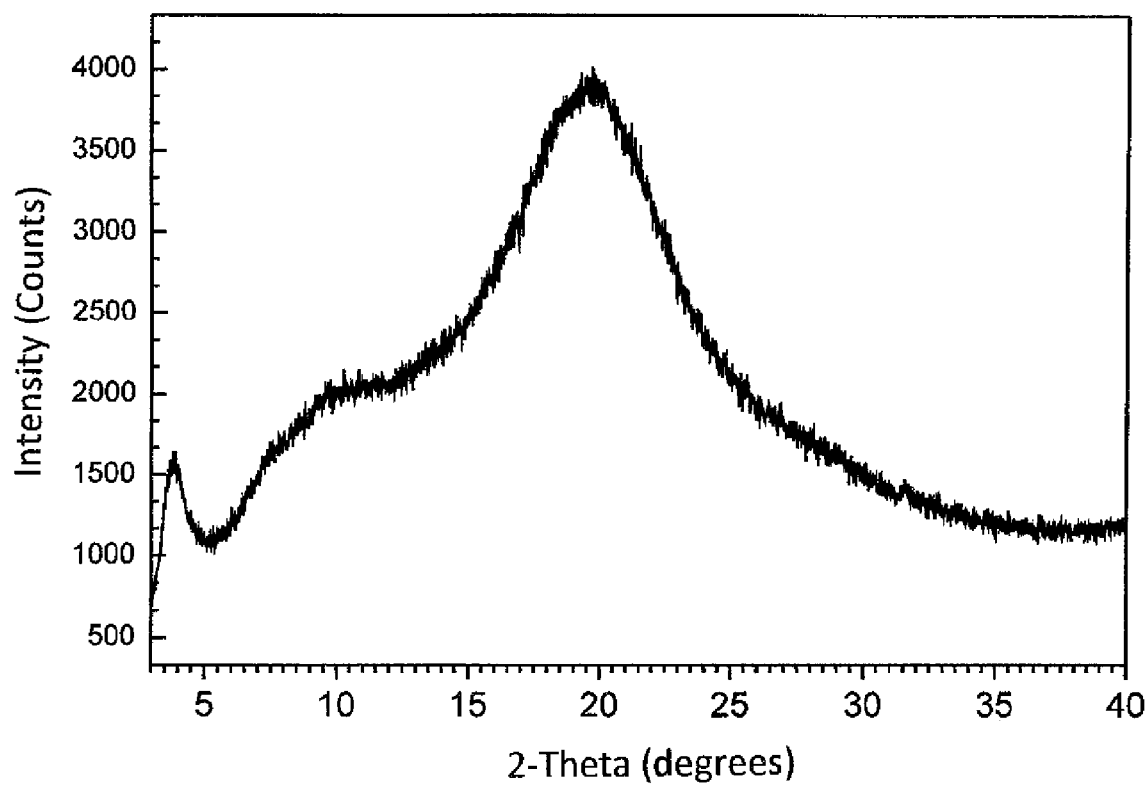
FIG. 3a. Rosuvastatin Calcium X-ray diffractogram.

For an X-Ray powder diffraction analysis (FIGS. 3a-3c), a comparative assay between rosuvastatin calcium sample (FIG. 3a), rosuvastatin lysine (FIG. 3b) and lysine monohydrate (FIG. 3c) was performed, where the lysine monohydrate reading showed that the new salt is not the sum of rosuvastatin and lysine (it would be a sum of peaks). This demonstrates the differentiation of the new rosuvastatin lysine salt.

The new rosuvastatin lysine salt was identified in detail through the performed analysis, also stability assays were conducted.

Stability Assays

Figure 4:
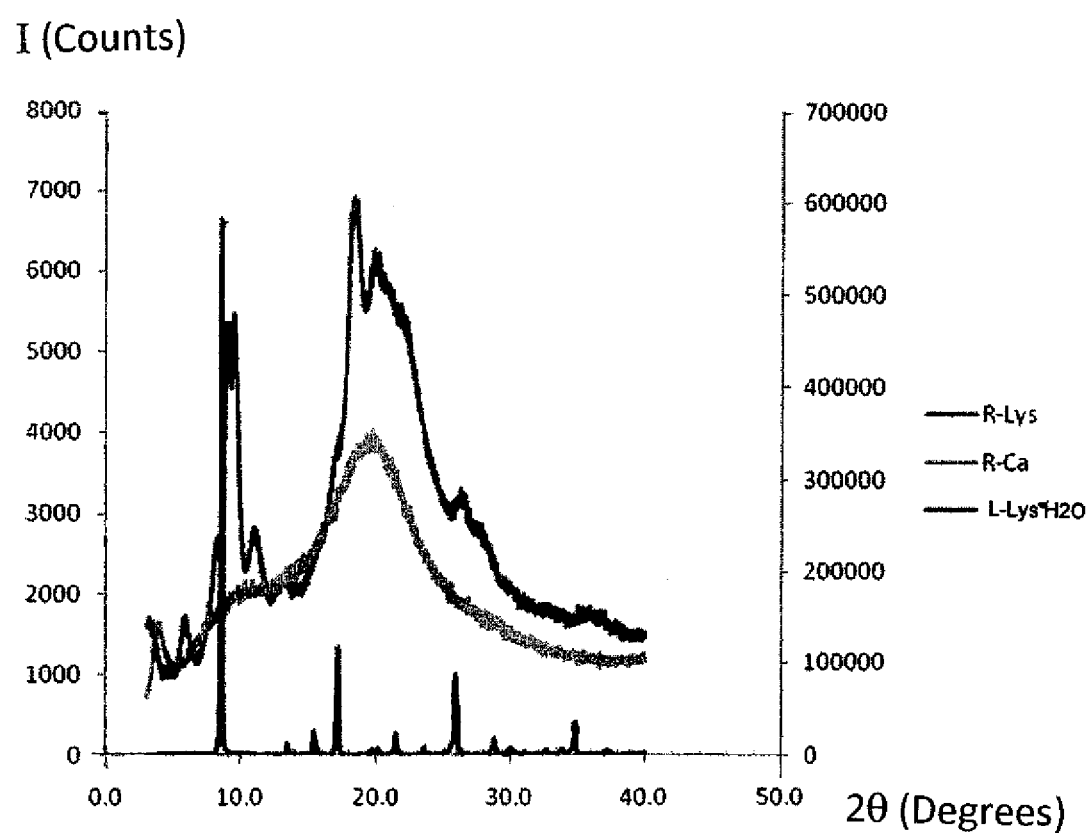
FIG. 4. X-ray diffractogram of rosuvastatin calcium, rosuvastatin lysine and lysine monohydrate at 30 days and 40° C.

An X-ray diffraction test was conducted for samples of rosuvastatin lysine (R-Lys), rosuvastatin calcium (R—Ca) and lysine monohydrate (L-Lys.H$_2$O) to verify their stability (FIG. 4). The samples were subjected to conditions of 40° C. for a 30-day period. The obtained results show a peak constant in the readings of the rosuvastatin-lysine sample, which indicates that this salt remains physically stable. The X-ray spectrum of FIG. 4 for rosuvastatin calcium (R—Ca) and rosuvastatin lysine (R-Lys) salts yield readings in a scale ranging from 0 to 8000 in intensity, however for L-lysine monohydrate (L-Lys-H2O) the X-Ray readings exhibits very high peak values which depart from the scale in thousand units, for this reason an enlarged scale on the right side of the vertical axis was placed.

Figure 5:
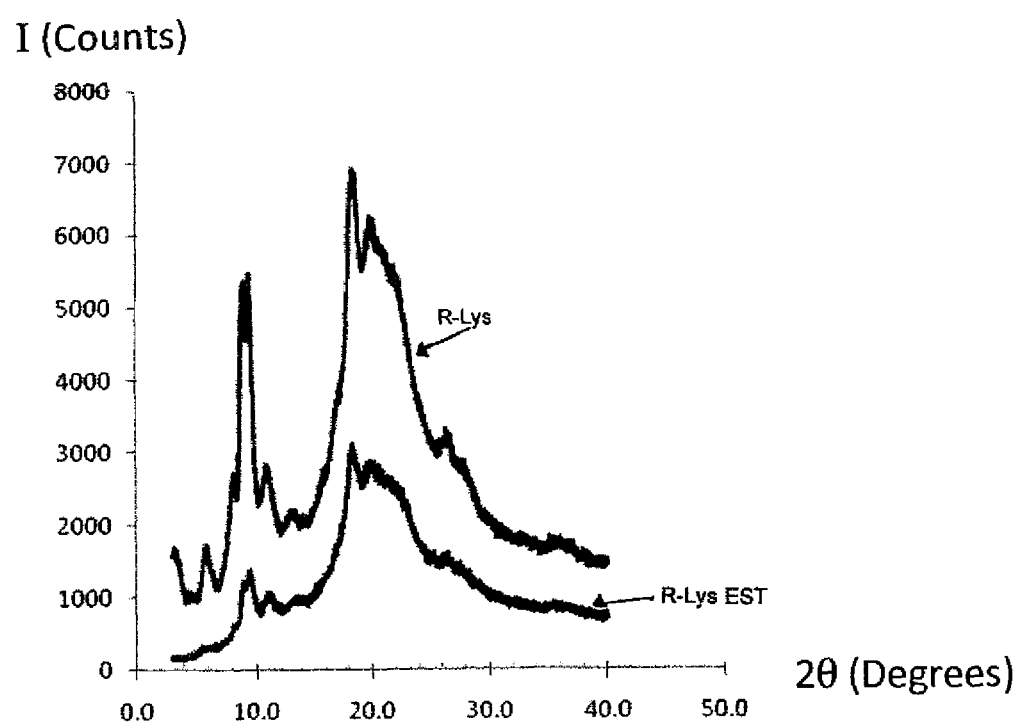
FIG. 5. Lysine rosuvastatin X-ray diffractogram at zero time and rosuvastatin lysine after being subjected to stability test under conditions of 40° C. for 30 days.

Additionally, the new salt of the present invention was subjected to an accelerated stability test at 40° C. for 30 days, then an X-ray diffraction test was carried out to this sample and it was compared with the X-ray diffraction analysis performed to the sample at the starting time. Results are shown in FIG. 5. The sample subjected to stability studies at 40° C. for 30 days is represented as R-Lys-EST, and the salt sample at zero time is represented as R-Lys. It can be verified that the new salt preserves its bond and integrity by exhibiting spectra with the same characteristic peaks, which shows that the rosuvastatin lysine salt is stable and can be used in the manufacture of a pharmaceutical composition.

Comparative Solubility Test

Additionally, a comparative solubility test was performed between rosuvastatin calcium and rosuvastatin lysine.

The following table shows the results obtained from the comparative solubility tests of the calcium salt and lysine salt, using different solvents.

| TEST | CALCIUM | LYSINE |
| --- | --- | --- |
| Description | Amorphous white to beige powder. Unctuous, without flowability. | Yellowish powder. Good flowability. |

-continued

| TEST | CALCIUM | LYSINE |
|---|---|---|
| SOLUBILITY | | |
| Water | 5.3 mg/mL | 218 mg/mL |
| Ethanol | 10 mg/mL (Taffy) | 40 mg/mL |
| Methanol | Taffy | 20 mg/mL |
| HCl 10% | It sticks to the bottom of the container. | |
| NaOH 10% | 0.6 mg/mL (Yellowish solution) | 1 mg/mL |

From the above table, it can be observed that the rosuvastatin lysine salt shows better solubility and flowability.

Rosuvastatin-lysine presents better solubility and in a preferred embodiment is useful in the manufacture of pharmaceutical compositions that comply with physicochemical stability, dissolution and bioavailability specifications.

Some non-limiting examples of the formulation are shown below.

FORMULATION 1 EXAMPLE 4.5 mg of rosuvastatin powder administered as rosuvastatin lysine salt, lactose (124.5 mg), microcrystalline cellulose (60 mg) and magnesium stereate (1 mg) are mixed, passed through a No. 40 sieve and filled in capsules.

FORMULATION 2 EXAMPLE 4.5 mg of rosuvastatin powder administered as rosuvastatin lysine sal, lactose (119.5 mg), microcrystalline cellulose (75 mg) and magnesium stereate (1 mg) are mixed and compressed with a tabletting machine, and taken to a 200 mg weight. Optionally, the tablet may be coated.

The formulation examples are non-limiting for use only with the rosuvastatin lysine salt, but with other amino acid salts such as histidine.

In addition to the advantages presented due to the use of rosuvastatin lysine salt, it is possible to prepare pharmaceutical compositions with other substances that can be selected from ascorbic acid, lactic acid, citric acid, among others.

The invention has been sufficiently described so that a person with average knowledge in the art may reproduce and obtain the results mentioned in this description. However, anyone skilled in the art corresponding to this invention may be able to make modifications not described in this application. Therefore, if the matter claimed matter in the following claims is required for the application of such modifications in a determined method, this method must be understood within the scope of the present invention.

The invention claimed is:

1. A (3R,5S,6E)-7-[4-(4-fluorophenyl)-2-(N-methylmethanesulfonamide)-6-(propan-2-yl)pyrimidin-5-yl]-3,5-dihydroxihept-6-enoic lysine salt of formula

Figure 3B:
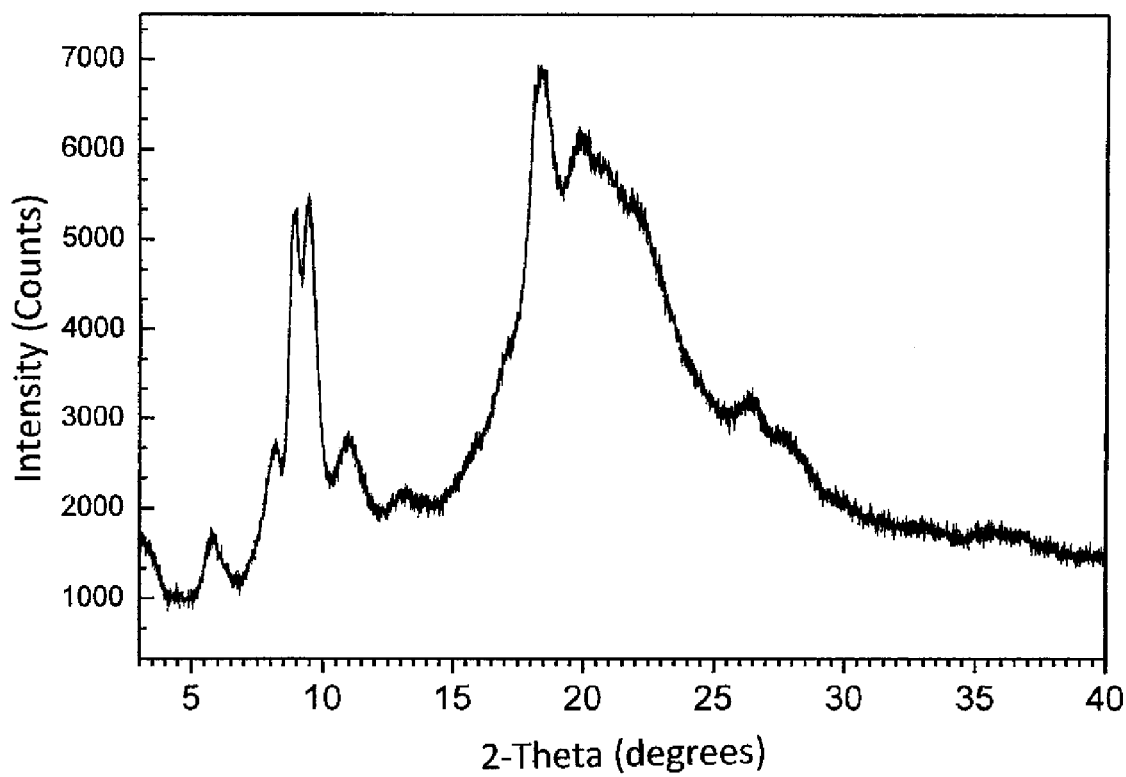
FIG. 3b. Rosuvastatin lysine X-ray diffractogram.
Figure 3C:
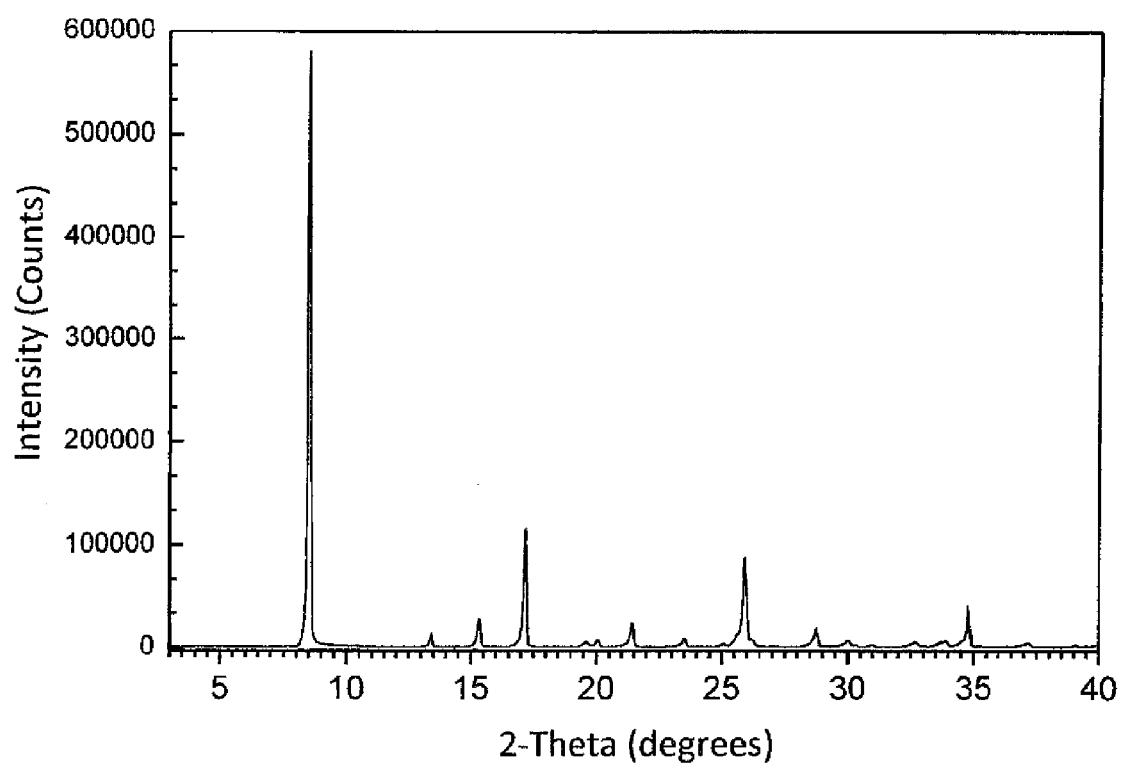
FIG. 3c. Rosuvastatin lysine monohydrate X-ray diffractogram.

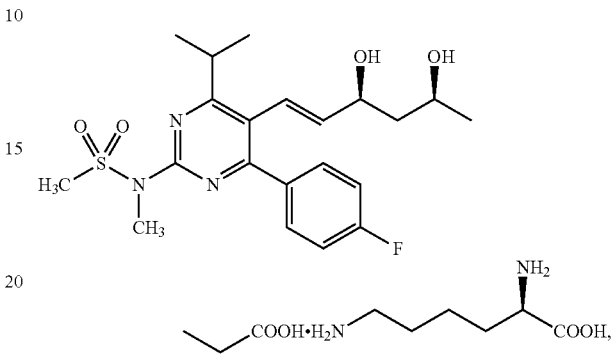

which shows an X-ray diffraction pattern (2θ) substantially similar to the one depicted in FIG. 3b.

2. A pharmaceutical composition comprising the salt of claim 1, in combination with a pharmaceutically acceptable carrier.

3. A method of manufacturing a pharmaceutical composition comprising the step of adding the salt of claim 1 to a pharmaceutically acceptable carrier.

4. The method according to claim 3, wherein the pharmaceutical compositions are in the form of tablets or capsules.

5. A method of manufacturing medicaments for the treatment of cardiovascular diseases comprising the step of adding the compound of claim 1 to a pharmaceutically acceptable carrier.

6. A process for synthesizing the rosuvastatin-lysine salt of claim 1, comprising the steps:
   a) subjecting the rosuvastatin calcium salt to a dissociation process; and
   b) mixing the acid rosuvastatin resulting from the previous step with an aqueous solution containing lysine monohydrate for forming the salt in the presence of a methanol/ethyl acetate solution.

* * * * *